United States Patent [19]
Curley, Jr.

[11] Patent Number: 5,808,111
[45] Date of Patent: Sep. 15, 1998

[54] STABLE ACITRETINOID COMPOUNDS

[75] Inventor: Robert W. Curley, Jr., Columbus, Ohio

[73] Assignee: The Ohio State Research Foundation, Columbus, Ohio

[21] Appl. No.: 851,632

[22] Filed: May 6, 1997

[51] Int. Cl.$^6$ .................. C07D 309/10; C07D 315/00
[52] U.S. Cl. .................. 549/417; 549/419; 549/420; 549/423
[58] Field of Search .................. 549/417, 419, 549/420, 423

[56] References Cited

U.S. PATENT DOCUMENTS

| | | | |
|---|---|---|---|
| 4,855,463 | 8/1989 | Barua et al. | 549/417 |
| 5,061,723 | 10/1991 | Barua et al. | 514/460 |
| 5,516,792 | 5/1996 | Curley, Jr. et al. | 514/459 |
| 5,574,177 | 11/1996 | Curley, Jr. et al. | 549/417 |
| 5,599,953 | 2/1997 | Curley, Jr. et al. | 549/417 |
| 5,663,377 | 9/1997 | Curley, Jr. et al. | 549/417 |

OTHER PUBLICATIONS

Abstract: "Cancer Chemopreventive Retinoid Metabolites: C–Glucuronide Analogues of 4–Hydroxphenylretinamide–O–Glucuronide" by Panigot et al., presented at the Fourth Chemical Congress of North America, in New York, New York on Aug. 25–30, 1991.

Abstract: "Preparation of C–Glucuronide Analogues of Retinoid O–Glucuronides and Their Preliminary in Vitro Breast Cancer" by Panigot et al., presented at the AAPS Annual Meeting and Exposition in San Antonio, Texas on Nov. 15–19, 1992.

"N–(4–Hydroxyphenly)retinamide, A New Retinoid for Prevention of Breast Cancer in the " by Moon et al., Cancer research 39, pp. 1339–1346, Apr. 1979.

"Structure–Activity Relationships of Retinoids in Hamster Tracheal Organ Culture" by Newton et al., Cancer Research 40, pp. 3413–3425, Oct. 1980 by Laboratory of Chemoprevention, National Cancer Institute, Bethesda, Maryland 20205.

"Chemoprevention of Breast Cancer With Retinoids" by Veronesi et al., Journal of the National Cancer Institute Monographs, No. 12, pp. 93–97, 1992.

"Chemical Synthesis of all–trans retinoyl β–glucuronide" by Barua et al., Journal of Lipid Research 26, pp. 1277–1282, 1985 by Department of Biochemistry and Biophysics, Iowa State University, Ames, IA 50011.

"Retinoids in Cancer Treatment" by Tallman et al., The Journal of Clinical Pharmacology 32, No. 10, pp. 868–888, Oct. 1992 by J.B. Lippincott Co., USA.

"Retinoids as Chemopreventive and Anticancer Agents in Intact Animals (Review)" by Hill et al., Anticancer Research 2, pp. 111–124, 1982 by Sourthern Research Institute, Box 3307–A, Birmingham, Alabama 35255.

"Growth Suppression of Human Breast Carcinoma Cells in Culture by N–(4–Hydroxyphenyl)retinamide and its Glucuronide and Through Synergism with Glucarate" by Bhatnagar et al., Biochemical Pharmacology, 41, No. 10, pp. 1471–1477, 1991 by Pergamon Press, Great Britain.

"Therapeutic effect of n–(4–Hydroxyphenyl)retinamide on N–methyl—N–nitrosourea–induced Rat Mammary Cancer" by Dowlatshahi et al., Cancer Letters 47, pp. 187–192, 1989 by Elsevier Scientific Publishers Ireland Ltd.

"Effects of Retinoid Glucuronides on Mammary Gland Development in Organ Culture" by Mehta et al., Oncology 48, pp. 505–509, 1991 by S.Karger AG, Basel, Switzerland.

"Putative Metabolites Derived from Dietary Combinations of Calcium Glucarate and N–(4–Hydroxphenyl)retinamide Act Synergistically to Inhibit the inductionof Rat Mammary Tumors by 7,12–dimethylbenz[α]anthracene" by Abou–Issa et al., Proc. Natl. Acad. Sci. USA 85, pp. 4181–4184, Jun. 1988.

"Effects of Pretreatment with the Retinoid N–(4–Hydroxphenyl)–all–trans–retinamide and phenobarbital on the Disposition and metabolism of N–(4–Hydroxyphenyl)–all–trans–retinamide in Mice" by Hultin et al., Drug Metabolism and Disposition 16, No. 6, pp. 783–788, 1988.

"Biotransformation and Biological Activity of N–(4–Hydroxyphenyl)retinamide Derivatives in Rodents" by Swanson et al., The Journal of Pharmacology and Experimental Therapeutics 219, No. 3, pp. 632–637, 1981.

"Teratogenicity of N–(4–Hydroxyphenyl)–all–trans–retinamide in Rats and Rabbits" by Kenel et al., Teratogensis, Carcinogenesis, and Mutagenesis 8, pp. 1–11, 1988.

"In vitro interaction of fenretinide with plasma retinol–binding protein and its functional consequences" by Berni et al., Federation of European Biochemical Societies 308, No. 1, pp. 43–45, 1992.

"Tolerability of the Synthetic Retinoid Fenretinide (HPR)" by Costa et al., European Journal of Clinical Oncology 25, No. 5, pp. 805–808, 1989 by Pergamon Press, Great Britain.

"Pharmacokinetics of N–4–Hydroxyphenyl–retinamide and the effect of its oral administration of plasma retinol concentrations in cancer patients" by Peng et al., Int. J. Cancer 43, pp. 22–26, 1989.

"Induction of Differentiation of Human promyelocytic Leukemia Cell Line HL–60 by Retinoyl Glucuronide, a Biologically Active Metabolite of Vitamin A" by Zile et al., Proc. Nat. Acad. Sci. USA 84, pp. 2208–2212, Apr. 1987 by Academic Press, Inc.

"Analysis of Water–Soluble Compounds: Glucuronides" By Barua, Arun B., Method Enzymol. 189, pp. 136–145, 1990.

(List continued on next page.)

Primary Examiner—Ba K. Trinh
Attorney, Agent, or Firm—Calfee Halter & Griswold LLP

[57] ABSTRACT

Novel acitretinamide compounds which are soluble and stable in water and useful in aqueous delivery systems, particularly to treat cancer, are provided. The novel acitretinamide compounds, 1-(D-glucopyranosyl)acitretinamide, 1-(D-glucopyranuronosyl)acitretinamide and the metal salts thereof, are hereinafter collectively referred to as the "acitretinamide compounds". The invention also relates to novel methods of making the acitretinamide compounds.

8 Claims, No Drawings

OTHER PUBLICATIONS

"Synthesis of the D–glucuronic acid conjugates of N–(4–hydroxyphenyl)–and N–(2–hydroxyenthly)–retinamides" by Dawson et la., *Carbohydrate Research* 85, pp. 121–129, 1980 by Elsevier Scientific Publishing Co.

"Amino–Substituted β–Benzyl–C–glycosides; Novel B–Glycosidase Inhibitors" by Schmidt et al., *Angew. Chem. Int. Ed. Engl.* 30, No. 10, pp. 1328–1329, 1991.

"The Effective Charges at the Active Sites of Two Glycosidases" by Loeffler et al., *J.C.S. Chem. Comm.*, pp. 984–985, 1974.

"A Review of the Methods of Chemical Synthesis of Sulphate and Glucuronide Conjugates" by Kaspersen et al., *Xenobiotica*, vol. 17, No. 12, pp. 1451–1471, 1987.

Hanessian, Stephen, et al., "Synthesis of Naturally Occuring C–Nucleosides, Their Analogues, and Functionalized C–Glycosyl Presursors," *Advances in Carbonydrate Chemistry and Biochemistry,* vol. 33, 1976.

"The Chemistry and Biochemistry of C–Nucleosides and C–Aryglycosides" edited by Ellis et al., in *Progress in Medicinal Chemistry 22,* published by Elsevier Science Publishers, B.V. (Biomed. Div.) Oxford, 1985.

"Recent Developments in Synthesis of C–Glycosides" by Postema, Maarten H.D., in *Tetrahedron Report No. 322,* Mar. 12, 1992.

Abstract: "New Syntheses of C–substituted carbohydrates and their derivatives", Yu, et al., Doklady Akad. Nauk, S.S.S.R. 129, 1049–52 (1959).

Abstract: "Preparation of glucopyranosylbenzene derivative" by Gerecs, et al. Acta. Chim. Acad. Sci. Hung. 13 231–2 (1957).

"N–Linked Analogs of Retinoid O–Glucuronides" by Robarge, et al., *Bioorganic & Medical Chemistry Letters,* vol. 4, No. 17, Aug. 1994, pp. 2117–2122.

"N–Linked Analogs of Retinoid O–Glucuronides" by Robarge, et al. (Abstract) Am. Chem. Society 25th Cent. Reg. Meeting, Oct. 4–6, 1993.

"Synthesis and Evaluation of N–Linded Glycoside Analogs of Retinoic Acid" by Robarge, et al., 27th Annual Mid–Atlantic. Sympos., Jul. 1994 (Abstract).

"Synthesis of N–Linked Glycoside Analogs of Retinoic Acid" by Robarge et al. Am. Chem. Soc., Aug. 21–25, 1994.

"N–and C–Glycoside Analogs of Retinoid O–Glucuronides and Their Breast Cancer Inhibitory Potential" by Panigot, et al., XIII Int. Symp. (Paris), Sep. 1994.

Biochemical Pharmacology, vol. 41, No. 10, issued 1991, Bhatnagar et al., "Growth Suppression of Human Breast Carcinoma Cells in Culture by N–(4–Hydroxy–phenyl) Retinamide and its Glucuronide and Through Synergism With Glucarate," pp. 93–97.

Journal of the National Cancer Institute Monographs, No. 12, issued 1992, Veronesi et al., "Chemoprevention of Breast Cancer With Retinoids," pp. 93–97.

Journal of Lipid Research, vol. 26, issued 1985, Barua et al., "Chemical Synthesis of All–Trans Retinoyl Betaglucuronide," pp. 1277–1282.

STABLE ACITRETINOID COMPOUNDS

BACKGROUND OF THE INVENTION

Breast cancer kills thousands of women annually. While surgical intervention has saved the lives of many women, radical and partial mastectomies often prove physically and emotionally debilitating. Indeed, surgery, even when combined with chemotherapy, may still expose the patient to the threat of possible recurrence. Thus, drugs that promote the prevention of breast cancer are desirable. N-(4-hydroxyphenyl) retinamide displays chemopreventive activity in breast cancer (Moon et al. *Cancer Res.* (1979) 39, 1339–1346), (Abou-Issa, H. M. et al. *Proc. Natl. Acad. Sci. USA* (1988) 85, 4181–4184). The glucuronide, N-(4-hydroxyphenyl)retinamide-O-glucuronide has an even greater antiproliferative activity and less toxicity in both MCF-7 human mammary cell tumor culture than the 4-HPR. (Bhatnagar, R. et al. *Biochem. Pharmacol.* (1991) 41, 1471–1477.)

However, the 4-HPR-O-glucuronide is unstable; it is hydrolyzed in acidic media and also by the enzyme β-glucuronidase. The propensity to acid hydrolysis may limit the clinical usefulness of 4-HPR-O-glucuronide since oral administration of the drug may reduce the total available concentration of the active drug.

It is desirable to have stable chemopreventive drugs, for the prevention and treatment of breast cancer, which resist acid hydrolysis.

SUMMARY OF THE INVENTION

The present invention provides novel acitretinamide compounds which are soluble and stable in water, resist acid hydrolysis and are useful in aqueous delivery systems, particularly to treat cancer. The novel acitretinamide compounds, 1-(D-glucopyranosyl) acitretinamide, 1-(D-glucopyranuronosyl) acitretinamide and the metal salts thereof, are hereinafter collectively referred to as the "acitretinamide compounds". The invention also relates to novel methods of making the acitretinamide compounds.

DETAILED DESCRIPTION OF THE INVENTION

The present invention provides acitretinamide compounds which are soluble and stable in aqueous delivery systems. Specifically, the compounds of the present invention include: 1-(D-glucopyranosyl)acitretinamide; 1-(D-glucopyranuronosyl)acitretinamide; and the sodium salts thereof; hereinafter collectively referred to as the "acitretinamide compounds". The acitretinamide compounds are useful in both veterinary and human applications.

The acitretinamide compounds which include both the alpha and beta epimers, have the following structure:

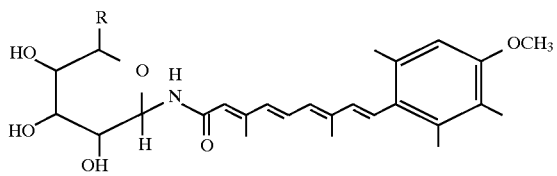

wherein:
R is $CH_2OH$, $COOH$, $COO^-M$;
M is a metal preferably selected from the group consisting of: sodium, lithium, potassium, calcium, where the metal forms a divalent cation, such as calcium, then two acitretinamide molecules are associated with each metal.

Method of Making the Acitretinamide Compounds

In the broadest sense the method for preparing the acitretinamide compounds comprises the steps of: providing a glycoside wherein all the hydroxy groups are protected with protecting groups; placing an azide group on the glycoside; then reducing the azide group to its corresponding amine; then retinoylating; and removing the protecting groups.

Preferably, to form 1-(β-D-glucopyranosyl) acitretinamide, the method generally involves first providing a protected 1-α-bromoglucose, in which the hydroxyl groups are protected, preferably in which they are protected with acetyl groups. The 1-α-bromoglucose, is then treated with sodium azide to form the 1-β-azido glucose. The azide group is then reduced using conventional techniques, such as, for example reducing in a hydrogen atmosphere over a palladium catalyst, to provide the 1-β-amino glucose. To this 1-β-amino glucose is added acitretinoyl chloride, preferably prepared in situ from acitretin and thionyl chloride, to give 1-(β-D-glucopyranosyl) acitretinamide. Finally, the protecting groups are removed, preferably by saponification to give 1-(β-D-glucopyranosyl) acitretinamide.

Preferably, to prepare 1-(D-glucopyranuronnosyl) acitretinamide, a similar method is followed as for the production of the 1-(β-D-glucopyranosyl) acitretinamide, except that the starting material is a protected 1-α-bromoglucuronide in which the carboxyl group is also protected with a methyl group, rather than the 1-α-bromoglucose. Also in preparing the 1-(D-glucopyranuronosyl) acitretinamide, after removing the hydroxyl protecting groups, the carboxyl protecting group is then removed to give the 1-(D-glucopyranuronosyl) acitretinamide.

In preparing the 1-(D-glucopyranuronosyl) acitretinamide it is difficult to eliminate the less preferred α-epimer. Thus, the 1-(D-glucopyranuronosyl) acitretinamide typically contains a mixture of the alpha and beta epimers. The alpha and beta epimers are shown below.

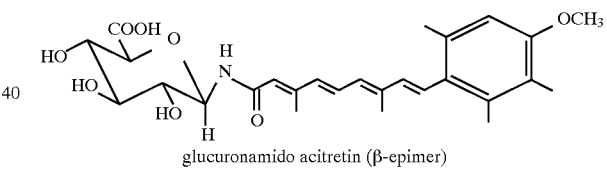

glucuronamido acitretin (β-epimer)

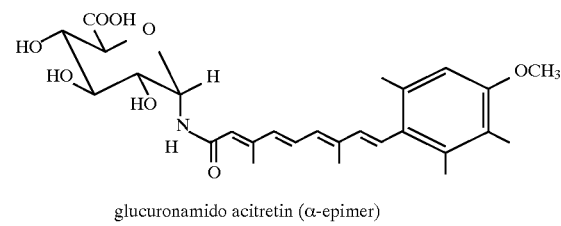

glucuronamido acitretin (α-epimer)

To form the metal salt of 1-(D-glucopyranosyl) acitretinamide, or 1-(D-glucopyranuronosyl) acitretinamide compounds, the compound is hydrolyzed, preferably by placing the compound in an alkaline aqueous solution. Preferably the aqueous alkaline solution contains sodium hydroxide to form the sodium salt thereof.

The acitretinamide compounds are preferably prepared according to the following examples.

PREPARATION OF THE ACITRETINOID COMPOUNDS

Example 1: Preparation of 1-(D-glucopyranosyl) acitretinamide

The 1-(D-glucopyranosyl) acitretinamide, also referred to herein as "glucosamido acitretin", was prepared by first preparing 2,3,4,6-tetra-O-acetylglucopyranosyl bromide. The 2,3,4,6-tetra-O-acetylglucopyranosyl bromide was prepared by dissolving 50 gm of glucose pentaacetate, available from Sigma Chemical Company, in 200 mL of 30% HBr/acetic acid; the mixture was allowed to stand overnight in the refrigerator. The solvent was removed under reduced pressure, the residue dissolved in $CHCl_3$ and the $CHCl_3$ solution was washed with $H_2O$, saturated $NaHCO_3$, saturated NaCl, and dried over $Na_2SO_4$. The drying agent was removed by filtration and the residue crystallized from ethanol. The acetobromoglucose has a melting point of 89° C.

Next, 8.22g, that is 20 mmol, of the 2,3,4,6-tetra-O-acetylglucopyranosyl bromide was dissolved in 250 ml of dimethylformamide and 2.6 g, that is, 40 mmol, or two equivalents of sodium azide was added. The mixture was stirred at room temperature for 24 hours and then poured into 500 ml of water. The organic soluble material was extracted three times with 150 ml ethyl acetate. The ethyl acetate extracts were washed twice with 100 ml water, then washed with saturated aqueous NaCl, dried over $MgSo_4$, and concentrated to dryness. The residue was recrystallized from ethanol to yield 6.1 g, that is, 82% of 2,3,4,6-tera-O-acetylglucopyranosyl azide. The 2,3,4,6-tetra-O-acetyl-β-D-glucopyranosyl azide had the melting point of 127°–129° C.

Next, 344 mg (0.924 mmol) of the 2,3,4,6-tetra-O-acetylglucopyranosyl azide was added to 50 mL of dry tetrahydrofuran containing 50 mg of 10% Pd on carbon. The solution was cooled to –15° C. and was shaken under 40 psi of hydrogen for 1 hour, filtered and concentrated to dryness to produce 2,3,4,6-tetra-O-acetylclucopyranosyl amine.

Acitretin was obtained by stirring the contents of thirty 25 mg capsules of etretinate in ethyl acetate for 4 days, filtering and concentrating to dryness to give recovery of greater than 90% of the theoretical quantity of etretinate. This etretinate was then dissolved in 20 ml of ethanol, 3 ml of 4N KOH, and enough acetone to make the solution one phase. The solution was stirred at room temperature for 2 ½ days, acidified to pH 3 with 3N HCl, and extracted with ethyl acetate. The ethyl acetate was washed with brine, dried over $Na_2SO_4$, filtered and concentrated to give a 69% yield of acitretin.

The acitretin was then used to prepare acitretinoyl chloride. 250 mg (0.77 mmol) of acitretin, 0.242 ml of pyridine, and 0.056 ml of thionyl chloride were combined in 20 ml of tetrahydrofuran at –78° C. After 1 hour, 320 mg (0.924 mmol) of 2,3,4,6-tetra-O-acetylglucopyranosyl amine was added in 10 ml of tetrahydrofuran containing 0.242 ml of pyridine and the resulting solution was maintained at –78° C. and stirred for 65 hours. The mixture was then diluted with 200 ml of ethyl acetate and extracted three times with 150 ml of $H_2O$ and brine. The organic layer was dried over $Na_2SO_4$, filtered, concentrated, treated with diazomethane, and chromatographed on silica gel with 1:1 ethyl acetate/hexane to remove traces of methyl acitretin, and yielded 406 mg (62%) of 2,3,4,6-tetra-O-acetylglucopyranosyl acitretinamide.

Next, 406 mg (0.48 mmol) of 2,3,4,6-tetra-O-acetylglucopyranosyl acitretinamide was dissolved in 20 ml of methanol and 0.2 g of $K_2CO_3$ was added. The mixture was stirred for 6 hours, filtered and concentrated to yield 215 mg (92% of 1-(β-D-glucopyranosyl)acitretinamide. The 1-(D-glycopyranosyl) acitretinamide was purified by chromatography on RP-8 with 80% methanol/$H_2O$.

Example 1A Preparation of 1-(D-glucopyranosyl) acitretinamide

The method of example 1 is followed, except that during the step of adding the acitretin, the temperature is raised to room temperature, to provide 1-(D-glycopyranosyl) acitretinamide which is a mixture of alpha and beta epimers.

Example 2 Preparation of 1-(D-glucopyranuronosyl) acitretinamide 1-(D-glucopyranuronosyl) acitretinamide, also referred to herein as "glucuronamido acitretin", was prepared by first preparing methyl-1,2,3,4-tetra-O-acetylglucuronate. The methyl-1,2,3,4-tetra-O-acetylglucuronate was prepared by dissolving 40 gm of glucurono-6,3-lactone, available from Aldrich Chemical Co., in 300 mL of $CH_3OH$ containing 100 mg NaOH and this was allowed to stand one hour. The solvent was removed under reduced pressure and the residue dissolved in 100 mL pyridine and 150 mL acetic anhydride; the mixture was stored in the refrigerator. The resulting solid methyl-1,2,3,4-tetra-O-acetylglucuronate was filtered and recrystallized from 95% ethanol. The methyl-1,2,4,5-tetra-O-acetyglucuronate has a melting point of 178° C.

Methyl 1-bromo-2,3,4-tetra-O-acetylglucuronate was prepared from methyl-1,2,3,4-tetra-O-acetlglucuronate. 50 g of methyl-1,2,3,4-tetra-O-acetylglucuronate was dissolved in 200 mL of 30% HBr/acetic acid; the mixture was allowed to stand overnight in the refrigerator. The solvent was removed under reduced pressure, the residue was dissolved in $CHCl_3$ and the $CHCl_3$ solution was washed with $H_2O$, saturated $NaHCO_3$, saturated NaCl and dried over $Na_2SO_4$. The drying agent was removed by filtration and the residue crystallized from ethanol. The methyl 1-bromo-2,3,4-tetra-O-acetylglucuronate had a melting point of 107° C.

Methyl 2,3,4,-tri-O-acetylglucopyranuronosyl bromide (7.94 g, 20 mmol) was dissolved in 250 ml of dimethylformamide and 2.6 g, that is 40 mmol of sodium azide was added. The mixture was stirred at room temperature for 24 hours and then poured into 500 ml of $H_2O$. The organic soluble material was extracted three times with 150 ml ethyl acetate. The combined ethyl acetate extracts were washed twice with 100 ml $H_2O$, brine, dried over $MgSO_4$, and concentrated to dryness. The residue was recrystallized from ethanol to yield 5.46 g (76%) of methyl 2,3,4,-tri-O-acetylglucopyranuronosyl azide. Methyl 2,3,4,-tri-O-acetylglucopyranuronosyl azide had the melting point of 152°–154°.

Next, 359 mg (1 mmol) of the methyl 2,3,4-tri-O-acetyl glucopyranuronosyl azide was added to 50 ml of tetrahyrofuran containing 50 mg of 10% Pd on carbon. The solution was cooled to –15° C. and was shaken under 40 psl of hydrogen for 1 hour, filtered and concentrated to dryness to produce methyl 2,3,4,-tri-O-acetylglucopyranuronosyl amine.

Acitretinoyl chloride was prepared from 250 mg (0.77) of acitretin, 0.242 ml of pryridine, and 0.056 ml of thionyl chloride in 20 ml of tetrahydrofuran at –78° C. After 1 hour, 333 ml (1 mmol) of methyl 2,3,4,-tri-O-acetylglucopyranuronosyl) amine was added in 10 ml of tetrahydrofuran containing 0.242 ml of pyridine and the resulting solution was maintained at –78° C. and stirred for 65 hours. The mixture was then diluted with 200 ml of ethyl acetate and extracted three times with 150 ml of $H_2O$ and brine. The organic layer was dried over $Na_2SO_4$, filtered, concentrated, treated with diazomethane, and chromatographed on silica gel with 1:1 ethyl acetate/hexane to remove traces of methyl acitretin, and yielded 385 mg (60%) of methyl 2,3,4-tri-O-acetylglucopyranuronosyl acitretinamide.

Next, 385 mg (0.6 mmol) of methyl 2,3,4,-tri-O-acetylglucopyranuronosyl acitretinamide was dissolved in 30 ml of methanol and 0.2 g of $K_2CO_3$ added. The mixture was stirred at room temperature for 6 hours and then 20 ml of 5N KOH added and then the solution stirred another 8 hours. The resulting suspension was taken to pH 3 with 3N HCl and extracted with ethyl acetate. The ethyl acetate was washed with brine, dried over $Na_2SO_4$, filtered and concentrated to yield 95 mg (65%) of 1-(D-glucopyranuronosyl) acitretinamide which was a 5:1 mixture of β/α epimers. The 1-(D-glycopyranuronosyl) acitretinamide, which is substantially all beta epimer, was purified by chromatography on RP-18 with 80% methanol/$H_2O$.

Example 3 1-(D-glycopyranuronosyl) acitretinamide

The procedure of example 2 was followed except that the acitretinoyl chloride was prepared from 250 mg (0.77) of acitretin, 0.242 ml of pryridine, and 0.056 ml of thionyl chloride in 20 ml of tetrahydrofuran at about 0° C. rather than at −78° C. to provide 1-(D-glycopyranuronosyl) acitretinamide. The 1-(D-glycopyranuronosyl) acitretinamide prepared according to this example was is about a 1:1 mixture of the alpha epimer to the beta epimer.

Example 4

To form the metal salt of the material of the compound of example 2 or 2A, the compound of example 2 or 2A is hydrolyzed by placing the compound in an alkaline aqueous solution containing sodium hydroxide to form the sodium salt thereof.

Stability of the Acitretinamide Compounds

To determine the relative stability of the 1-(D-glucopyranuronosyl) acitretinamide toward hydrolysis, samples of N-(4-hydroxyphenyl)retinamide-O-glucuronide as a control and 1-(D-glucopyranuronosyl)acitretinamide from example 2, were each separately dissolved in 1:1 methanol/0.01N HCl solution. The 1:1 methanol/0.01N HCl solution has a pH of about 1–2, which approximates the pH of gastric juices. Aliquots of each these solutions were removed periodically and analyzed by high performance liquid chromatography for the decomposition of the retinoid.

After two hours, the N-(4-hydroxyphenyl)retinamide-O-glucuronide had undergone approximately 20% solvolysis. In contrast, the 1-(D-glucopyranuronosyl)acitretinamide remained intact.

By 8 hours, approximately 47% of the 0-glucuronide had degraded while only 20% of the N-glucuronide, the 1-(D-glucopyranuronosyl)acitretinamide had degraded. The resistance of the 1-(D-glucopyranuronosyl)acitretinamide toward acid hydrolysis, indicates that it does not hydrolyze in vivo.

Evaluation of the Acitretinamide Compounds

Human MCF-7 mammary tumor cells were plated at a concentration of 3–5×$10^4$ cells/wells in a 24 well plate in Eagle's minimal essential media containing 10% fetal bovine serum (charcoal stripped twice) and gentamycin, and without phenol red. On days 4 and 6 the media was replaced with fresh media containing either: glucosamido acitretin from example 1; glucuronamido acitretin, from example 2; or glucuronamido acitretin from example 3; so that the final volume was 1.5 mL. Positive control cultures containing acitretin, and untreated control cultures were also prepared.

On day 8 1μCi of $^3$H-thymidine was added to each well in 10 μL of media, and incubated at 37° C. for 2 hours. The media was removed, the cells were washed and harvested into 12×75 mm test tubes using trypsin—EDTA. The cells were washed twice with phosphate buffered saline, 1 mL of 5% trichloroacetic acid was added at 4° C., and incubated overnight at 4° C.

At day 9, the tubes were centrifuged at 1500×g, the supernatant was decanted, 1 mL 0.1N NaOH and 1% Triton N101 were added to the pellet then the pellet was vortex mixed. Next, the entire 1 mL was added to 5 mL of liquid scintillation cocktail with 115 μL of 1N HCL added to each vial. The number of radioactive disintegrations/minute were counted. The results are presented below in Table I. The work was repeated with glucuronamido acitretin from example 2 and example 3; the results are also shown in Table I.

TABLE I

Inhibition of MCF-7 cell growth with glucuronamido acitretin and glucosamido acitretin

| | Untreated | Acitretin positive control | | | Glucosamido Acitretin Example 1 | | |
|---|---|---|---|---|---|---|---|
| | Control | 0.1 nM | 10 nM | 1 μM | 0.1 nM | 10 nM | 1 μM |
| 6 hr | 17336.90 | 12427.07 | 16051.33 | 4022.99 | 9648.27 | 53696.91 | 29419.36 |
| Dpm | 4867.33 | 12262.64 | 10721.61 | 6600.22 | 10725.10 | 45168.25 | 19861.47 |
| 3H | 322.21 | 10823.98 | 9189.97 | 2656.13 | 9147.40 | 39818.76 | 18862.17 |
| thymidine | 16006.56 | 9426.65 | 8471.81 | 5540.53 | 8182.37 | 30154.16 | 34665.77 |
| | 18963.68 | 11391.22 | 10326.43 | 6694.11 | 10840.32 | 29436.48 | 37211.86 |
| | 21083.60 | 10229.00 | 10418.00 | 4798.91 | | 37650.72 | 32388.44 |
| Avg | 17330.05 | 11093.43 | 10863.19 | 5052.19 | 9708.69 | 39320.88 | 28734.85 |
| Std Dev. | 2189.80 | 1067.11 | 2447.50 | 1425.67 | 996.20 | 8422.48 | 7036.33 |
| % control | 100.00% | 64.01% | 62.67% | 29.15% | 56.02% | 226.89% | 165.81% |
| Std. Dev. | 12.64% | 6.16% | 14.12% | 8.23% | 5.75% | 48.60% | 40.60% |

| | Untreated | Glucuronamido Acitretin (1:1 ratio β:α isomers) (example 3) | | | Glucuronamido Acitretin (5:1 ratio β:α isomers) (example 2) | | |
|---|---|---|---|---|---|---|---|
| | Control | (0.1 nM) | (10 nM) | (1 μM) | (0.1 nM) | (10 nM) | (1 μM) |
| 96 hr | 17336.90 | 11917.33 | 15656.91 | 11784.20 | 4654.91 | 9868.52 | 2162.27 |
| Dpm | 4867.33 | 10881.60 | 10854.44 | 8876.14 | 5282.33 | 10291.41 | 3172.69 |

TABLE I-continued

Inhibition of MCF-7 cell growth with glucuronamido acitretin and glucosamido acitretin

| 3H | 322.21 | 13404.54 | 12363.58 | 10649.43 | 7967.10 | 13463.60 | 1040.58 |
|---|---|---|---|---|---|---|---|
| thymidine | 16006.56 | 9874.54 | 9950.19 | 13133.61 | 5409.31 | 7973.05 | 1554.42 |
|  | 18963.68 | 13312.29 | 9146.11 | 2769.02 | 10039.86 | 11208.90 | 3652.15 |
|  | 21083.60 | 5958.72 | 5181.22 | 23918.39 | 2145.69 | 8069.21 | 6923.37 |
| Avg 1 | 17330.05 | 10891.49 | 10525.24 | 11855.13 | 5916.53 | 10145.78 | 3084.25 |
| Std Dev. | 2189.80 | 2536.23 | 3178.30 | 6325.18 | 2505.90 | 1882.78 | 1933.74 |
| % control | 100.00% | 62.85% | 60.73% | 68.41% | 34.14% | 58.54% | 17.80% |
| Std Dev. | 12.65% | 14.63% | 18.34% | 36.50% | 14.46% | 10.86% | 11.16% |
| Avg 2 |  | 111878.05 | 11594.05 | 11110.85 | 5828.41 |  | 2316.42 |
| Std Dev. |  | 1370.84 | 2295.14 | 1561.39 | 1267.37 |  | 974.63 |
| % control |  | 68.54% | 66.90% | 64.11% | 33.63% |  | 13.37 |
| Std. Dev. |  | 7.91% | 13.24% | 9.01% | 7.31% |  | 5.62% |

As can be seen from Table I the glucuronamido acitretin of example 3, reduced the average cellular proliferation to about 62 to 68 percent of the control values. The glucuronamido acitretin of example 2 reduced the average cellular proliferation to about 17.8 to 58 percent of the control values in one experiment and to about 13.6 to 33 percent of the control values, in the second experiment. The glucosamido acitretin of example 1 reduced the average proliferation to about 58 percent of control values, at the dosage of 1 nM; the results are not the same at the higher dosages.

The acitretinamide compounds are administered to patients using conventional techniques such as, injection, topical, or oral administration. The acitretinamide compounds are preferably administered in ranges from 1 mg to about 1000 mg, preferably 200 to 800, preferably on a regular basis, more preferably on a daily basis. The acitretinamide compounds are administered in pharmacologically acceptable carriers; where the acitretinamide compound is injected, it is preferably in an aqueous pharmacologically suitable carrier, such as, for example, saline, or distilled water. Where the acitretinamide compound is administered orally, the compound is preferably compounded into a conventional form such tablet, capsule or liquid using conventional compounding ingredients. Where the acitretinamide compound is administered topically, it is preferably compounded into a conventional form such as lotion, cream, gel, liquid or the like.

The acitretinamide compounds of the present invention while described as useful for slowing the growth of tumor cells, are also useful for experimental and research purposes.

What is claimed is:

1. A compound having the following structure:

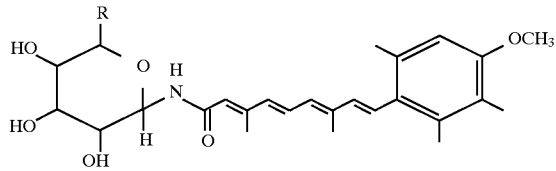

wherein R is $CH_2OH$, COOH, $COO^-M^+$ and M is a metal.

2. The compound of claim 1, wherein R is COOH.

3. The compound of claim 1, wherein R is $CH_2OH$.

4. The compound of claim 1, wherein R is $COO^-M^+$.

5. A method for preparing an acitretinamide compound, comprising the steps of:

A. providing a glycoside wherein all the hydroxy groups are protected with protecting groups;

B. placing an azide group on the glycoside;

C. reducing the azide group on the product of step B to its corresponding amine;

D. acitretinoylating the product of step C; and

E. removing the protecting groups on the product of step D.

6. The method of claim 5, wherein the acitretinamide compound is 1-(D-glucopyranosyl) acitretinamide, wherein the protected glycoside is glucose pentaacetate, and the deprotection of step E is accomplished by deacetylating the product of step D.

7. The method of claim 5, wherein the acitretinamide compound is 1-(D-glucopyranuronosyl) acitretinamide, wherein the glycoside is acetylglucuronate and the deprotection of step E is accomplished by deacetylating and demethylating the product of step D.

8. The method of claim 7, wherein the acitretinamide compound is the metal salt of 1-(D-glucopyranuronosyl) acitretinamide, wherein the 1-(D-glucopyranuronosyl) acitretinamide, is hydrolyzed in presence of an alkaline, metal hydroxide solution to form the metal salt of 1-(D-glucopyranuronosyl)acitretinamide.

\* \* \* \* \*